US006821755B2

(12) United States Patent
Werner et al.

(10) Patent No.: US 6,821,755 B2
(45) Date of Patent: Nov. 23, 2004

(54) PREPARATION OF A RECOMBINANT PROTEIN IN A PROKARYOTIC HOST CELL

(75) Inventors: Rolf-Günther Werner, Biberach (DE); Klaus Bergemann, Biberach (DE); Friedrich Götz, Tübingen (DE); Andreas Peschel, Tübingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 09/916,229

(22) Filed: Jul. 27, 2001

(65) Prior Publication Data

US 2003/0017531 A1 Jan. 23, 2003

Related U.S. Application Data

(60) Provisional application No. 60/229,010, filed on Aug. 30, 2000.

(30) Foreign Application Priority Data

Jul. 27, 2000 (DE) .......................................... 100 37 111

(51) Int. Cl.[7] .......................... C12P 21/02; C12N 1/21; C12N 15/10
(52) U.S. Cl. .............. 435/71.2; 435/252.3; 435/252.33; 435/252.8; 435/69.4; 435/69.7
(58) Field of Search .......................... 435/71.2, 252.3, 435/252.33, 252.8, 69.4, 69.7

(56) References Cited

U.S. PATENT DOCUMENTS 5,840,533 A * 11/1998 Niwa et al. ................. 435/69.1
6,270,988 B1   8/2001 Brinkmann et al. ....... 435/69.1

FOREIGN PATENT DOCUMENTS

| EP | 81306193 | * | 7/1982 |
| EP | 0 373 365 B1 | | 6/1990 |
| WO | WO 98/35029 A1 | | 8/1998 |
| WO | WO 00/44926 A1 | | 8/2000 |

OTHER PUBLICATIONS

Makrides, Strategies for achieving high–level expression of genes in *escherichia coli*, 1996, Microbiological Reviews, pp. 512–538.*
Hua et al., Enhancement of expression of human granulocyte–macrophage colony stimulating factor by argu gene product in *escherichia coli*, 1994, Biochemistry and Molecular Biology International, vol. 32, pp. 537–543.*
Johansen et al., High–level production of fully active human alpha1–antitrypsin in *escherichia coli*, 1987, Mol. Biol. Med., vol. 4, pp. 291–305.*
Pikaart et al., Expression and codon usage optimization of the erythroid–specific transcription factor cGaTA–1 in baculoviral and bacterial systems, 1996, Protein Expression and Purification, vol. 8, pp. 469–475.*

Makoff et al., Expression of tetanus toxin fragment in *E.coli*: high level expression by removing rare codons, 1989, Nucleic Acid Research, vol. 17, pp. 10191–10202.*
Hale et al., Codon optimization of the gene encoding a domain from human type 1 neurofibromin protein results in a threefold improvement in expression level in *escherichia coli*, 1998, Protein Expression and Purification, vol. 12, pp. 185–188.*
Ruhikanta et al., Hyperexpression of rat spermatidal protein TP2 in *escherichia coli* by codon optimization and engineering the vector–encoded 5' UTR, 1998, Protein Expression and Purification, vol. 13, pp. 184–190.*
George et al., High–level expression in *escherichia coli* of biologically active bovine growth hormone, 1985, DNA, vol. 4, pp. 273–281.*
Kane, Effects of rare codon clusters on high–level expression of heterologous proteins in *escherichia coli*, 1995, Current Opinion in Biotechnology, vol. 6, pp. 494–500.*
Gotz et al., Complete nucleotide sequence of the lipase gene from *staphylococcus hyicus* cloned in *staphylococcus carnosus*, 1985, Nucleic Acid Research, vol. 13, pp. 5895–5906.*
Gotz et al., *Staphyloccus carnosus*: a new host organism for gene cloning and protein production, 1990, Journal of Applied Bacteriology Symposium Supplement, pp. 49s–53s.*
Pschorr et al., Production of the immunoglobulin variable domain REIv via a fusion protein synthesized and secreted by *staphyloccus carnosus*, 1994, Biol. Chem. Hoppe–Seyler, vol. 375, pp. 271–280.*
Wada et al., Codon usage tabulated from the GenBank genetic sequence data, 1992, Nucleic Acids Research, vol. 20, pp. 2111–2118.*
Ikehara et al., Synthesis of a gene gor human growth hormone and its expression in *escherichia coli*, 1984, Proc. Natl. Sci. USA, vol. 81, pp. 5956–5960.*
Kanaya, S., et al., "Studies of codon usage and tRNA genes of 18 unicellular organisms and quantification of *Bacillus subtilis* tRNAs: gene expression level and species–specific diversity of codon usage based on multivariate analysis," *Gene* 238:143–155, Elsevier Science B.V. (Sep. 1999).
Liljeqvist, S., et al., "Surface display of functional fibronectin–binding domains on *Staphylococcus carnosus*," *FEBS Lett.* 446:299–304, Amsterdam Elsevier Science B.V. (Mar. 1999).
Nakamura, Y., et al., "Codon usage tabulated from international DNA sequence databases: status for the year 2000," *Nucleic Acids Res.* 28:292, Oxford University Press (Jan. 2000).

(List continued on next page.)

*Primary Examiner*—James Ketter
*Assistant Examiner*—Daniel Sullivan
(74) *Attorney, Agent, or Firm*—Sterne, Kessler, Goldstein & Fox P.L.L.C.

(57) ABSTRACT

The invention relates to advantageous processes for preparing heterologous proteins in prokaryotic host cells by improved codon use and/or expression of tRNAs which code for codons occurring rarely in said host cell.

88 Claims, 4 Drawing Sheets

OTHER PUBLICATIONS

Figure 1:
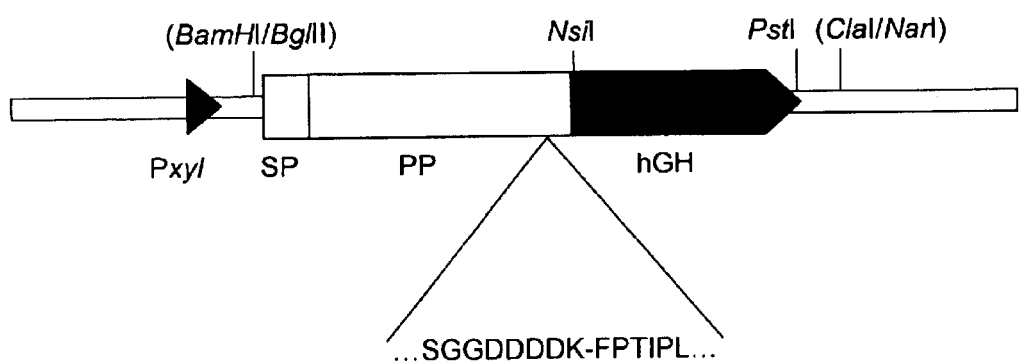

Sturmfels, A., et al., "Secretion of human growth hormone by the food–grade bacterium *Staphylococcus carnosus* requires a propeptide irrespective of the signal peptide used," *Arch. Microbiol.* 175:295–300, Springer–Verlag (Apr. 2001).

Williams, D.P., et al., "Design, synthesis and expression of a human interleukin–2 gene incorporating the codon usage bias found in highly expressed *Escherichia coli* genes," *Nucleic Acids Res.* 16:10453–10467, Oxford University Press (1988).

Brinkman, U. et al., "High–level expression of recombinant genes in *Escherichia coli* is dependent on the availability of the dnaY gene product," *Gene* 85:109–114, Elsevier Science Publishers B.V. (Biomedical Division) (1989).

Del Tito, Jr., B.J. et al., "Effects of a Minor Isoleucyl tRNA on Heterologous Protein Translation in *Escherichia coli,*" *J. Bacteriol.* 177:7086–7091, American Society for Microbiology (1995).

Makrides, S.C., "Strategies for Achieving High–Level Expression of Genes in *Escherichia coli,*" *Microbiol. Rev.* 60:512–538, American Society for Microbiology (1996).

Nikoleit, K. et al., "Comparative biochemical and molecular analysis of the *Staphylococcus hyicus, Staphylococcus aureus* and a hybrid lipase," *Eur. J. Biochem.* 228:732–738, Springer International and the Federation of European Biochemical Societies (1995).

Peschel, A. et al., "Inducible production and cellular location of the epidermin biosynthetic enzyme EpiB using an improved staphylococcal expression system," *FEMS Microbiol. Lett.* 137:279–284, Elsevier Science B.V. and the Federation of European Microbiological Societies (1996).

Schenk, P.M. et al., "Improved High–Level Expression System for Eukaryotic Genes in *Escherichia coli* Using T7 RNA Polymerase and Rare $^{Arg}$tRNAs," *BioTechniques* 19:196–200, Eaton Publishing Co. (1995).

Wong, S.–L., "Advances in the use of *Bacillus subtilis* for the expression and secretion of heterologous proteins," *Curr. Opin. Biotechnol.* 6:517–522, Current Biology (1995).

\* cited by examiner

```
      BglII            NdeI
  1 NNAGATCTAAAGGAGGTAATTCATATGAAAGAAACAAAAACATCAACACACATTTCTATCCGTAAGTCGGCTTATGGTGC
  1                    M  K  E  T  K  H  Q  H  T  F  S  I  R  K  S  A  Y  G  A

81 CGCGTCGGTTATGTCGCATCATGTATATTGTCATCGGTGGGGCCGTGGCAGAGGCAAATGATTCGACAACACAAACAA
 20  A  S  V  M  V  A  S  C  I  F  V  I  G  G  G  V  A  E  A  N  D  S  T  T  Q  T

161 CGACACCACTAGAAGTCGCTCAAACGTCGCAGCAAGACATACAGAAACATCAAACACCTGTTACATCATTACATACTGCA
 47  T  T  P  L  E  V  A  Q  T  S  Q  Q  E  T  H  T  H  Q  T  P  V  T  S  L  H  T  A

241 ACACCTGAACATGTTGATGACTCTAAAGAAGCAACACCTTTACCTGAAAAAGCAGAGTCACCAAAAACCGAAGTGACAGT
 74  T  P  E  H  V  D  D  S  K  E  A  T  P  L  P  E  K  A  E  S  P  K  T  E  V  T  V

321 TCAACCTTCATCGCATACAGAGGTACCTGCCTTGACATAAAAACACAGCAACAACCGGCGTATAAGGATAAAACGG
100  Q  P  S  S  H  T  Q  E  V  P  A  L  H  K  K  T  Q  Q  P  A  Y  K  D  K  T

401 TACCAGAGTCAACGATAGCATCAAAGTCGGTTGAATCAAATAAGCAACAGAAAATGAGATGTCACCTGTTGAACATCAT
127  V  P  E  S  T  I  A  S  K  S  V  E  S  N  K  A  T  E  N  E  M  S  P  V  E  H  H

481 GCTTCAAATGTGGAAAAACGTGAAGATAGATTGGAGACTAATGAGACAACCGCCATCAGTGACCGTGAATTTAGCCA
154  A  S  N  V  E  K  R  E  D  R  L  E  T  N  E  T  T  P  P  S  V  D  R  E  F  S  H

561 TAAAATCATCAATAATACGCACGTAAATCCAAAAACGGATGACAAACAAACGTTAATGTTGATACGAAAACGATAGACA
180   K  I  I  N  N  T  H  V  N  P  K  T  D  G  Q  T  N  V  N  V  D  T  K  T  I  D

641 CCGTTTCACCGAAAGATGACAGAATAGATACGGCCGAAACCAAGTCGACGTTCCTAAAGAAAATACAACGGCACAA
207  T  V  S  P  K  D  D  R  I  D  T  A  Q  P  K  Q  V  D  V  P  K  E  N  T  T  A  Q
                                                          NsiI
721 AATAAATTTACATCACAAGCGAGCGACAAAAAGAAGCCAACAGTAAAGATGCATCAGGTGGTGATGATGATAAATTTCC
234  N  K  F  T  S  Q  A  S  D  K  K  P  T  V  K  D  A  S  G  G  D  D  D  K  F  P
```

Fig. 3A

```
              BfrI
 801 AACAATTCCCTTAAGTCGATTGTTCGATAACGCTATGTTACGTGCACATAGATTACACCAGCTAGCATTCGATACTTATC
 260   T  I  P  L  S  R  L  F  D  N  A  M  L  R  A  H  R  L  H  Q  L  A  F  D  T  Y

881 AAGAATTTGAGGAAGCTTACATCCCAAAGAACAAAGTATAGCTTTTTACAAATCCGCAAACATCATTATGTTTCTCT
 287   Q  E  F  E  E  A  Y  I  P  K  E  Q  K  Y  S  F  L  Q  N  P  Q  T  S  L  C  F  S

961 GAATCAATTCCAACACTAGTAACCGTGAGGAAACTCAGCAAAAATCAAATTTAGAACTTTTACGTATTAGCTTGTTACT
 314   E  S  I  P  T  P  S  N  R  E  E  T  Q  Q  K  S  N  L  E  L  L  R  I  S  L  L  L

1041 TATACAATCTTGGTTAGAACCAGTTCAATTTTTACGTTCAGTATTCCAAATAGTTTAGTCTATGGTGCTTCAGACTCTA
 340   I  Q  S  W  L  E  P  V  Q  F  L  R  S  V  F  A  N  S  L  V  Y  G  A  S  D  S

1121 ACGTATACGATTATTGAAAGACTTAGAAGAAGGAATTCAAACATTAATGGGTCGTTTGGAAGATGGTTCACCAAGAACT
 367   N  V  Y  D  L  L  K  D  L  E  E  G  I  Q  T  L  M  G  R  L  E  D  G  S  P  R  T

1201 GGCCAAATTTTAAAACAAATATAGCAAATTCGATACTAATTCACATAACGATGACCATTACTAAAAATTACGGTTT
 394   G  Q  I  F  K  Q  T  Y  S  K  F  D  T  N  S  H  N  D  D  A  L  K  N  Y  G  L

1281 ATTGTATTGTTTCGTAAAGATATGATGGATAAAGTTGAAACATTCTTACGCATAGTACAATGCCGTTCTGTTGAAGGATCAT
 420   L  Y  C  F  R  K  D  M  D  K  V  E  T  F  L  R  I  V  Q  C  R  S  V  E  G  S
                                                        PstI
1361 GTGGTTTTTAATGATAACTGCAG
 447   C  G  F  *  *  *  *
```

Fig. 3B

PREPARATION OF A RECOMBINANT PROTEIN IN A PROKARYOTIC HOST CELL

The instant application claims the benefit of provisional U.S. Appl. No. 60/229,010, filed Aug. 30, 2000, which is herein incorporated by reference and DE 100 37 111.6, filed July 27, 2000 (in the German language), which is herein incorporated by reference.

The present invention relates to advantageous processes for preparing heterologous proteins in prokaryotic host cells by improved codon use and/or expression of tRNAs which code for rarely occurring codons in the said host cell. Numerous bacteria, particularly Gram-positive bacteria, for example, have already been used as host cells for the preparation of heterologous recombinant proteins, e.g. secreted proteins, in an endotoxin-free environment (references 8, 9, 19). The bacterium *Staphylococcus carnosus* (*S. carnosus*), for example, which is used in the food industry for the fermentation of meat and fish, is a suitable bacterium for this purpose. It is free from virulence factors and proteolytic activities in the supernatant and is capable of secreting large amounts of protein (10). Moreover, only small amounts of host cell-coded proteins are secreted, which makes it easier to purify the protein produced. Bacterial enzymes (7, 4, 17), for example, have already been recombinantly produced and expressed in *S. carnosus*. Recombinant *S. carnosus* strains which express antigens such as the Streptococcus protein G on their surface, are particularly promising as live vaccines (5, 12).

One crucial disadvantage of numerous bacterial systems is their use of rare codons, which is very different from the codon preference in human genes. The presence of rare codons in *E. coli* led to delayed and reduced expression of recombinant genes (2, 6). The problem of the present invention is therefore to overcome this disadvantage of the prior art and provide a prokaryotic expression system with improved properties.

DESCRIPTION OF THE INVENTION

The problem is solved within the scope of the claims and specification of the present invention.

The use of the singular or plural in the claims or specification is not intended to be limiting in any way and also includes the alternative form.

The invention relates to a process for preparing a heterologous recombinant protein in a prokaryotic host cell, characterized in that the codon use of the host cell for host cell genes is determined, in the nucleic acid coding for the heterologous recombinant protein in the host cell rarely occurring codons are replaced by frequent codons, said host cell is transformed with said nucleic acid coding for the recombinant protein and said recombinant nucleic acid is expressed. With a process according to the invention it is possible to achieve a significantly better expression rate of the heterologous proteins compared with the process known from the prior art. The processes according to the invention are also particularly advantageous for the expression of recombinant proteins on the surface of prokaryotes, as the covalent anchoring on the cell wall depends on intact C-termini, which are absent from the secreted truncated proteins which are not prepared by the process according to the invention.

By heterologous is meant that said protein in said prokaryotic host cell is not native, i.e. it occurs as a protein peculiar to the host cell. "Recombinant" means produced by molecular-biological methods. A heterologous recombinant protein may be any protein known to the skilled person, such as, for example, insulin, hGH, tPA, cytokines, such as e.g. interleukins (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumour necrosis factor (TNF), TNF alpha and TNF beta, TRAIL; G-CSF, GM-CSF, M-CSF, MCP-1 and VEGF. Prokaryotic host cells may be any host cells known to the skilled person, particularly Gram-positive and Gram-negative host cells. These may be, for example, *Escherichia coli, Bacillus subtilis, Streptomyces, Proteus mirabilis* or preferably Staphylococcus, such as e.g. *Staphylococcus carnosus* in particular, as available from public collections, e.g. the Deutsche Sammlung von Mikroorganismen und Zellkulturen GmbH, Braunschweig, Germany, e.g. Strain TM300 (DSM 4600, 4601 or 4602).

Within the scope of the process according to the invention, first of all the use of the codons, i.e. the coding nucleotide triplets, is analysed for said host cell for as many native proteins as possible in the basic coding gene sequence. The codon frequencies of 51 genes were analysed for the host organism *Staphylococcus carnosus* Strain TM300 (10) by way of example and are shown in the following Table 1:

TABLE 1

| Amino acid | Codon | Frequency In *S. carnosus* (%) |
|---|---|---|
| A (Ala) | GCA | 49.0 |
|  | GCT | 32.0 |
|  | GCG | 12.3 |
|  | GCC | 6.7 |
| C (Cys) | TGT | 72.7 |
|  | TGC | 27.3 |
| D (Asp) | GAT | 79.4 |
|  | GAC | 20.6 |
| E (Glu) | GAA | 90.4 |
|  | GAG | 9.6 |
| F (Phe) | TTT | 53.7 |
|  | TTC | 46.3 |
| G (Gly) | GGT | 53.9 |
|  | GGA | 22.6 |
|  | GGC | 16.4 |
|  | GGG | 7.1 |
| H (His) | CAT | 75.8 |
|  | CAC | 24.2 |
| I (Ile) | ATT | 61.7 |
|  | ATC | 27.6 |
|  | ATA | 10.7 |
| K (Lys) | AAA | 88.1 |
|  | AAG | 11.9 |
| L (Leu) | TTA | 57.2 |
|  | TTG | 18.8 |
|  | CTT | 12.0 |
|  | CTA | 4.9 |
|  | CTG | 5.6 |
|  | CTC | 1.5 |
| M (Met) | ATG | 100 |
| N (Asn) | AAT | 64.9 |
|  | AAC | 35.1 |
| P (Pro) | CCA | 43.5 |
|  | CCT | 31.3 |
|  | CCG | 23.0 |
|  | CCC | 2.2 |
| Q (Gln) | CAA | 89.4 |
|  | CAG | 10.6 |
| R (Arg) | CGT | 54.9 |
|  | AGA | 20.9 |
|  | CGC | 12.2 |
|  | CGA | 10.3 |
|  | AGG | 0.8 |
|  | CGG | 0.8 |
| S (Ser) | TCA | 33.9 |
|  | TCT | 27.7 |
|  | AGT | 21.0 |

TABLE 1-continued

| Amino acid | Codon | Frequency In S. carnosus (%) |
|---|---|---|
| | AGC | 12.2 |
| | TCC | 2.5 |
| | TCG | 2.7 |
| T (Thr) | ACA | 52.6 |
| | ACT | 32.8 |
| | ACG | 10.5 |
| | ACC | 4.1 |
| V (Val) | GTT | 36.7 |
| | GTA | 36.7 |
| | GTG | 13.6 |
| | GTC | 12.9 |
| W (Trp) | TGG | 100 |
| Y (Tyr) | TAT | 76.4 |
| | TAC | 23.6 |
| * (Stop) | TAA | 68.6 |
| | TAG | 19.6 |
| | TGA | 11.8 |

It was found that coding sequences of Staphylococci for example have a very low G+C content of about 30% and the A+T-rich codons are preferred. Therefore according to the invention the production of recombinant proteins, for example hGH, is increased in two ways: (i) exchanging rare codons in the coding gene sequence for frequent ones (cf. also Example 1) and/or (ii) expressing rare tRNAs (tRNA= transfer RNA; cf. also Example 2).

The invention therefore also relates to processes for preparing a heterologous recombinant protein, wherein for S. carnosus, as shown in Table 1, or in similar manner for every other host cell according to the invention, either some or all of the rarely occurring codons are replaced by frequent ones, for example according to the analysis in Table 1 the Glu codon GAG is replaced by GAA or the Leu-codons CTC, CTG and CTA are replaced by TTA, TTG or CTT.

The invention therefore further relates to a process for preparing a heterologous recombinant protein in a prokaryotic host cell, characterised in that the codon use of the host cell for host cell genes is determined, said host cell is transformed with the nucleic acid which codes tRNA or tRNAs specific for rarely occurring codons and with said nucleic acid coding for the recombinant protein, and said recombinant nucleic acid is expressed (cf. also Example 2). The skilled person can determine the rare codons of the host cell by analyzing the genes or the cDNAs (or by reverse transcription of the mRNA). This has been done, for example, for the host cell S. carnosus Strain TM300 (10) in Table 1. The invention includes the introduction of tRNAs or nucleic acid coding therefore, for one to all the rare tRNAs in the host cell. Because the host cell is equipped with tRNAs which are specific for rare codons, the heterologous recombinant protein according to the invention is expressed in larger amounts than is the case in known processes from the prior art. This surprisingly advantageous property of the process according to the invention is also shown in Example 2. This may occur either on its own or in conjunction with the nucleic acid coding for the heterologous protein.

Therefore the invention includes a preferred process according to the invention which is characterized in that, in the nucleic acid coding for the heterologous recombinant protein in the host cell, rarely occurring codons are replaced by frequent codons and said host cell is transformed with tRNA or tRNAs coding for rarely occurring codons and with said nucleic acid coding for the recombinant protein.

The invention includes a preferred process according to the invention which is characterized in that codons which are used in the host cell with an average frequency of less than 15% are replaced by codons with an average frequency of at least 15%; preferably characterized in that codons which are used in the host cell with an average frequency of 7 to 12% are replaced by codons with an average frequency of more than 12%; most preferably characterized in that codons which are used in the host cell with an average frequency of up to 7 or 10% are replaced by codons with an average frequency of more than 7% or more than 10%. Another preferred embodiment is a preferred process according to the invention which is characterized in that the codon or codons which occur least often in said host cell is replaced by the codon or codons which occur most frequently in said host cell. One exception may be if said codons are absolutely essential for the expression.

The invention further includes a preferred process according to the invention which is characterized in that in the coding nucleic acid codons which are used in the host cell with an average frequency of less than 10% are replaced by codons with an average frequency of at least 10%.

The invention further includes a preferred process according to the invention which is characterized in that the host cell is Escherichia coli, as available from public collections, e.g. the Deutsche Sammlung von Mikroorganismen und Zellkulturen GmbH, Braunschweig, Germany, e.g. E. coli Strain K12 JM107 (DSM 3950).

The invention further includes a preferred process according to the invention which is characterized in that the host cell is a host cell selected from the genus Staphylococcus.

The invention further includes a preferred process according to the invention which is characterized in that the host cell is Staphylococcus carnosus (cf. also Examples 1 and 2).

In a preferred process according to the invention the recombinant protein is an antibody protein. By antibody protein is also meant a fragment, e.g. a Fab fragment (in English "Fragment antigen-binding=Fab"), a F(ab')$_2$ fragment, an Fv fragment (in English: "fragment variable"= fragment of the variable part) or a single-chain Fv (scFv)), minibodies, dia-, tria- and tetrabodies.

In a preferred process according to the invention the recombinant protein is insulin.

In a preferred process according to the invention the recombinant protein is tissue plasminogen activator (tPa).

In a preferred process according to the invention the recombinant protein is a human protein.

In a preferred process according to the invention the recombinant protein is growth hormone.

In a particularly preferred process according to the invention the recombinant protein is human growth hormone (hGH, cf. Examples 1 and 2).

Another preferred process according to the invention is characterized in that G- or C-rich codons are replaced by codons containing A or T. This means that codons which contain more G or C are replaced by codons which now contain, for example, an A or a T instead of a G or C; it does not mean that the codons must now contain exclusively G or C (cf. the most preferred embodiments hereinafter).

In the process according to the invention all the rare codons found may be replaced by frequent ones (cf. e.g. Table 1) and not only those specified in the preferred embodiments given hereinafter.

Another particularly preferred process according to the invention is characterized in that the codon GCC is replaced by GCA.

Another particularly preferred process according to the invention is characterized in that the codon TGC is replaced by TGT.

Another particularly preferred process according to the invention is characterized in that the codon GAC is replaced by GAT.

Another particularly preferred process according to the invention is characterized in that the codon GAG is replaced by GAA.

Another particularly preferred process according to the invention is characterized in that the codon TTC is replaced by TTT.

Another particularly preferred process according to the invention is characterized in that the codon GGG is replaced by GGT.

Another particularly preferred process according to the invention is characterized in that the codon CAC is replaced by CAT.

Another particularly preferred process according to the invention is characterized in that the codon ATA is replaced by ATT.

Another particularly preferred process according to the invention is characterized in that the codon AAG is replaced by AAA.

Another particularly preferred process according to the invention is characterized in that the codon CTC is replaced by TTA.

Another particularly preferred process according to the invention is characterized in that the codon AAC is replaced by AAT.

Another particularly preferred process according to the invention is characterized in that the codon CCC is replaced by CCA.

Another particularly preferred process according to the invention is characterized in that the codon CAG is replaced by CAA.

Another particularly preferred process according to the invention is characterized in that the codon CGG is replaced by CGT.

Another particularly preferred process according to the invention is characterized in that the codon TCG is replaced by TCA.

Another particularly preferred process according to the invention is characterized in that the codon ACC is replaced by ACA.

Another particularly preferred process according to the invention is characterized in that the codon GTC is replaced by GTT.

Another particularly preferred process according to the invention is characterized in that the codon TAC is replaced by TAT.

Another particularly preferred process according to the invention is characterized in that the codon TGA is replaced by TAA.

Yet another preferred process according to the invention is characterized in that the host cell is transformed with the nucleic acid coding for AGG-tRNA or AGA-tRNA and with said nucleic acid coding for the recombinant protein.

The invention also particularly includes a nucleic acid molecule coding for a recombinant heterologous protein, characterized in that at least one codon rarely occurring in the host cell has been replaced by a codon which occurs frequently in the host cell. By way of example the codons for the host cell *S. carnosus* were analysed in Table 1. The invention includes nucleic acid molecules wherein for *S. carnosus* or similarly for every other host cell according to the invention either some or all of the rarely occurring codons are replaced by frequent ones, for example the Glu codon GAG is replaced by GAA or the Leu codons CTC, CTG and CTA are replaced by TIA, TTG or CTT.

The invention includes a nucleic acid molecule coding for a recombinant heterologous protein, characterized in that codons which are used in the host cell with an average frequency of less than 15% are replaced by codons with an average frequency of at least 15%; preferably characterized in that codons which are used in the host cell with an average frequency of 7 to 12% are replaced by codons with an average frequency of more than 12%; most preferably characterized in that codons which are used in the host cell with an average frequency of up to 7 or 10% are replaced by codons with an average frequency of more than 7% or more than 10%. Another preferred embodiment is a nucleic acid molecule coding for a recombinant heterologous protein, characterized in that the codon or codons which occur least often in said host cell is or are replaced by the codon or codons occurring most frequently in said host cell. One exception may be if said codons are absolutely necessary for the expression.

The invention therefore relates in a preferred embodiment to a nucleic acid molecule, characterized in that codons which are used in the host cell with an average frequency of less than 10% are replaced by codons with an average frequency of at least 10%.

The invention further relates to a nucleic acid molecule according to the invention, characterized in that it codes for the human growth hormone hGH.

The invention relates to a nucleic acid molecule, characterized in that it comprises a nucleotide sequence from the following group: the following sequence

```
NNAGATCTAAAGGAGGTAATTCATATGAAAGAAACAAAACATCAACACACATTTTCTATCCGTAAGTCGGCTTATGGTGCCGCGTC

GGTTATGGTCGCATCATGTATATTTGTCATCGGTGGGGGCGTGGCAGAGGCAAATGATTCGACAACACAAACAACGACACCACTAG

AAGTCGCTCAAACGTCGCAGCAAGAAACACATACACATCAAACACCTGTTACATCATTACATACTGCAACACCTGAACATGTTGAT

GACTCTAAAGAAGCAACACCTTTACCTGAAAAAGCAGAGTCACCAAAAACCGAAGTGACAGTTCAACCTTCATCGCATACACAGGA

AGTACCTGCGTTACATAAAAAAACACAGCAACAACCGGCGTATAAGGATAAAACGGTACCAGAGTCAACGATAGCATCAAAGTCGG

TTGAATCAAATAAAGCAACAGAAAATGAGATGTCACCTGTTGAACATCATGCTTCAAATGTGGAAAAACGTGAAGATAGATTGGAG

ACTAATGAGACAACACCGCCATCAGTGGACCGTGAATTTAGCCATAAAATCATCAATAATACGCACGTAAATCCAAAAACGGATGG

ACAAACAAACGTTAATGTTGATACGAAAACGATAGACACCGTTTCACCGAAAGATGACAGAATAGATACGGCGCAACCGAAACAAG

TCGACGTTCCTAAAGAAAATACAACGGCACAAAATAAATTTACATCACAAGCGAGCGACAAAAAACCAACAGTAAAAGATGCATCA

GGTGGTGATGATGATGATAAATTTCCAACAATTCCCTTAAGTCGATTGTTCGATAACGCTATGTTACGTGCACATAGATTACACCA

GCTAGCATTCGATACTTATCAAGAATTTGAGGAAGCTTACATCCCAAAAGAACAAAAGTATAGCTTTTTACAAAATCCGCAAACAT
```

-continued

```
CATTATGTTTCTCTGAATCAATTCCAACACCTAGTAACCGTGAGGAAACTCAGCAAAAATCAAATTTAGAACTTTTACGTATTAGC

TTGTTACTTATACAATCTTGGTTAGAACCAGTTCAATTTTTACGTTCAGTATTCGCAAATAGTTTAGTCTATGGTGCCTCAGACTC

TAACGTATACGATTTATTGAAAGACTTAGAAGAAGGAATTCAAACATTAATGGGTCGTTTGGAAGATGGTTCACCAAGAACTGGCC

AAATTTTTAAACAAACATATAGCAAATTCGATACTAATTCACATAACGATGACGCATTACTTAAAAATTACGGTTTATTGTATTGT

TTTCGTAAAGATATGGATAAAGTTGAAACATTCTTACGCATAGTACAATGCCGTTCTGTTGAAGGATCATGTGGTTTTTAATGATA

ACTGCAG
```

(SEQ:ID-NO.1) or a partial sequence thereof, a nucleic acid which can hybridise with said sequence under stringent conditions, an allelic variant or a functional variant of said sequence or a variant of the nucleic acid on the basis of the degenerative code. N within the scope of the invention denotes any nucleotide known to the skilled person.

The invention further relates to a nucleic acid molecule coded by the nucleotide sequence of SEQ:ID-NO.1 according to the invention.

The invention relates to a vector containing a nucleic acid molecule according to the invention.

Another important embodiment of the invention is a host cell containing a nucleic acid molecule according to the invention or a vector according to the invention.

```
NNAGATCTAAAGGAGGTAATTCATATGAAAGAAACAAAACATCAACACACATTTTCTATCCGTAAGTCGGCTTATGGTGCCGCGTC

GGTTATGGTCGCATCATGTATATTTGTCATCGGTGGGGCGTGGCAGAGGCAAATGATTCGACAACACAAACAACGACACCACTAG

AAGTCGCTCAAACGTCGCAGCAAGAAACACATACACATCAAACACCTGTTACATCATTACATACTGCAACACCTGAACATGTTGAT

GACTCTAAAGAAGCAACACCTTTACCTGAAAAAGCAGAGTCACCAAAAACCGAAGTGACAGTTCAACCTTCATCGCATACACAGGA

AGTACCTGCGTTACATAAAAAAACACAGCAACAACCGGCGTATAAGGATAAAACGGTACCAGAGTCAACGATAGCATCAAAGTCGG

TTGAATCAAATAAAGCAACAGAAAATGAGATGTCACCTGTTGAACATCATGCTTCAAATGTGGAAAAACGTGAAGATAGATTGGAG

ACTAATGAGACAACACCGCCATCAGTGGACCGTGAATTTAGCCATAAAATCATCAATAATACGCACGTAAATCCAAAAACGGATGG

ACAAACAAACGTTAATGTTGATACGAAAACGATAGACACCGTTTCACCGAAAGATGACAGAATAGATACGGCGCAACCGAAACAAG

TCGACGTTCCTAAAGAAAATACAACGGCACAAAATAAATTTACATCACAAGCGAGCGACAAAAAACCAACAGTAAAAGATGCATCA

GGTGGTGATGATGATGATAAATTTCCAACAATTCCCTTAAGTCGATTGTTCGATAACGCTATGTTACGTGCACATAGATTACACCA

GCTAGCATTCGATACTTATCAAGAATTTGAGGAAGCTTACATCCCAAAAGAACAAAAGTATAGCTTTTTACAAAATCCGCAAACAT

CATTATGTTTCTCTGAATCAATTCCAACACCTAGTAACCGTGAGGAAACTCAGCAAAAATCAAATTTAGAACTTTTACGTATTAGC

TTGTTACTTATACAATCTTGGTTAGAACCAGTTCAATTTTTACGTTCAGTATTCGCAAATAGTTTAGTCTATGGTGCTTCAGACTC

TAACGTATACGATTTATTGAAAGACTTAGAAGAAGGAATTCAAACATTAATGGGTCGTTTGGAAGATGGTTCACCAAGAACTGGCC

AAATTTTTAAACAAACATATAGCAAATTCGATACTAATTCACATAACGATGACGCATTACTTAAAAATTACGGTTTATTGTATTGT

TTTCGTAAAGATATGGATAAAGTTGAAACATTCTTACGCATAGTACAATGCCGTTCTGTTGAAGGATCATGTGGTTTTTAATGATA

ACTGCAG
```

The abovementioned nucleic acid molecule according to the invention codes for hGH with the amino acid sequence of SEQ:ID-NO.2

Another important embodiment of the invention is a host cell containing one or more tRNA molecules which codes for codons occurring rarely in this host cell.

```
MKETKHQHTFSIRKSAYGAASVMVASCIFVIGGGVAEANDSTTQTTTPLEVAQTSQQETHTHQTPVTSLHTATPEHVDDSKEATPL

PEKAESPKTEVTVQPSSHTQEVPALHKKTQQQPAYKDKTVPESTIASKSVESNKATENEMSPVEHHASNVEKREDRLETNETTPPS

VDREFSHKIINNTHVNPKTDGQTNVNVDTKTIDTVSPKDDRIDTAQPKQVDVPKENTTAQNKFTSQASDKKPTVKDASGGDDDDKF

PTIPLSRLFDNAMLRAHRLHQLAFDTYQEFEEAYIPKEQKYSFLQNPQTSLCFSESIPTPSNREETQQKSNLELLRISLLLIQSWL

EPVQFLRSVFANSLVYGASDSNVYDLLKDLEEGIQTLMGRLEDGSPRTGQIFKQTYSKFDTNSHNDDALLKNYGLLYCFRKDMDKV

ETFLRIVQCRSVEGSCGF
```

A host cell of the genus Staphylococcus is preferred, while *Staphylococcus carnosus*, e.g. Strain TM300 (DSM 4600, 4601 or 4602) is most preferred.

The following Examples are intended to make the invention easier to understand and should in no way be regarded as limiting the scope of the invention.

EXAMPLE 1

Construction of a Synthetic hgH Gene with *S. carnosus*-specific Condon Use

As an example of a protein, human growth hormone (hGH) was expressed in *S. carnosus* Strain TM300.

Comparison of the codon use of the mature hGH with that shown in *S. carnosus* showed that 51 of the codons of the mature hGH, which represent 27% of the total number of codons, make up only 7% or less of the *S. carnosus* codon frequency (Tab. 2). An enterokinase cutting site was introduced at the 5' end of the DNA sequence of the mature hGH and the hGH was synthesised with *S. carnosus*-specific codon use. The codons in the synthetic gene were used in about the same frequency as in the *S. carnosus* gene. Codons which were used by *S. carnosus* in a frequency of less than 10% were not used, apart from those which were needed to introduce restriction cutting sites (cf. Tab. 2).

TABLE 2

Number of codons in hGH cDNA and in the synthetic hGH DNA according to the invention

| Amino Acid | Codon | 1 | 2 |
|---|---|---|---|
| A (Ala) | GCA | 1 | 4 |
|  | GCT | 1 | 3 |
|  | GCG | 0 | 0 |
|  | GCC | 5 | 0 |
| C (Cys) | TGT | 2 | 3 |
|  | TGC | 2 | 1 |
| D (Asp) | GAT | 2 | 8 |
|  | GAC | 9 | 3 |
| E (Glu) | GAA | 6 | 12 |
|  | GAG | 8 | 2 |
| F (Phe) | TTT | 4 | 7 |
|  | TTC | 9 | 6 |
| G (Gly) | GGT | 0 | 5 |
|  | GGA | 0 | 2 |
|  | GGC | 5 | 1 |
|  | GGG | 3 | 0 |
| H (His) | CAT | 1 | 2 |
|  | CAC | 2 | 1 |
| I (Ile) | ATT | 2 | 5 |
|  | ATC | 6 | 1 |
|  | ATA | 0 | 2 |
| K (Lys) | AAA | 1 | 8 |
|  | AAG | 8 | 1 |
| L (Leu) | TTA | 1 | 17 |
|  | TTG | 0 | 5 |
|  | CTT | 1 | 3 |
|  | CTA | 4 | 1 |
|  | CTG | 12 | 0 |
|  | CTC | 8 | 0 |
| M (Met) | ATG | 3 | 3 |
| N (Asn) | AAT | 0 | 5 |
|  | AAC | 9 | 4 |
| P (Pro) | CCA | 2 | 5 |
|  | CCT | 0 | 1 |
|  | CCG | 1 | 1 |
|  | CCC | 5 | 1 |
| Q (Gln) | CAA | 2 | 11 |
|  | CAG | 11 | 2 |
| R (Arg) | CGT | 1 | 7 |
|  | AGA | 0 | 2 |
|  | CGC | 4 | 1 |

TABLE 2-continued

Number of codons in hGH cDNA and in the synthetic hGH DNA according to the invention

| Amino Acid | Codon | 1 | 2 |
|---|---|---|---|
|  | CGA | 0 | 1 |
|  | AGG | 5 | 0 |
|  | CGG | 1 | 0 |
| S (Ser) | TCA | 3 | 8 |
|  | TCT | 3 | 4 |
|  | AGT | 1 | 3 |
|  | AGC | 6 | 3 |
|  | TCC | 4 | 0 |
|  | TCG | 1 | 0 |
| T (Thr) | ACA | 5 | 6 |
|  | ACT | 1 | 4 |
|  | ACG | 1 | 0 |
|  | ACC | 3 | 0 |
| V (Val) | GTT | 0 | 3 |
|  | GTA | 0 | 3 |
|  | GTG | 4 | 0 |
|  | GTC | 3 | 1 |
| W (Trp) | TGG | 1 | 1 |
| Y (Tyr) | TAT | 3 | 5 |
|  | TAC | 5 | 3 |
| * (Stop) | TAA | 0 | 2 |
|  | TAG | 1 | 0 |
|  | TGA | 0 | 1 |

[1] number of codons in hGH cDNA
[2] number in synthetic hGH DNA (according to the invention)

Figure 2:
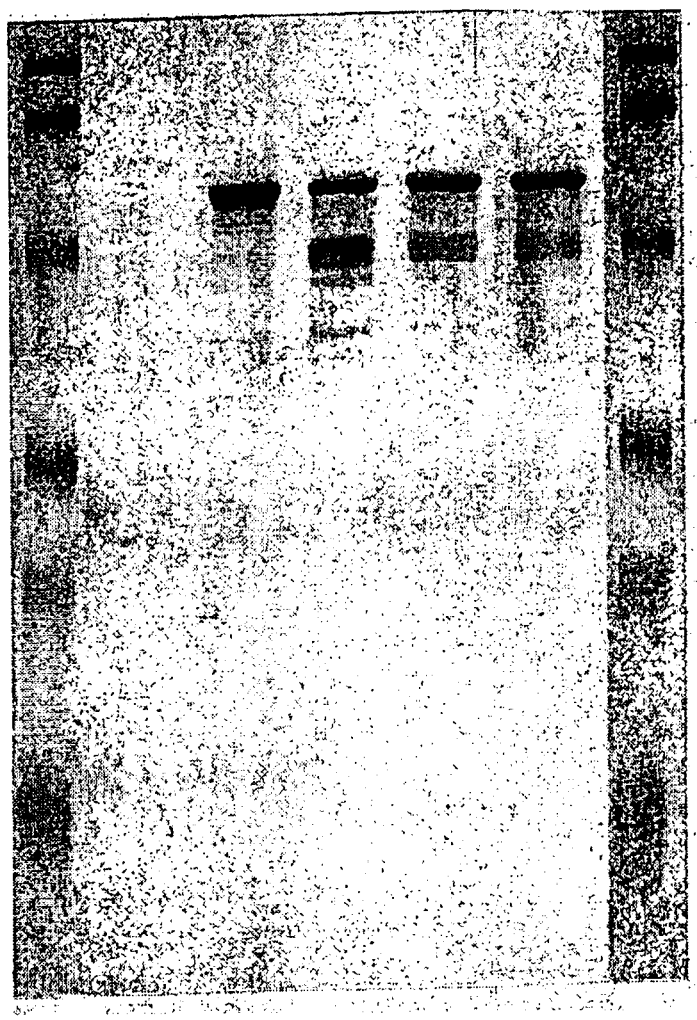

The synthetic hGH DNA sequence was synthesised from overlapping oligonucleotides which were hybridised and ligated in vitro. The resulting DNA fragment was cloned into the *E. coli* plasmid pSL1190 (3), verified by sequencing and inserted in the hGH expression cassette in order to replace the hGH cDNA between the NsiI and PstI cutting sites (FIG. 1). The new expression cassette was isolated as a BglII-ClaI fragment, cloned into the compatible BamHI and NarI cutting sites of the Staphylococci-expression vector pTX15 and transformed in *S. carnosus* TM300 by protoplast transformation. In the expression vector obtained, the lip-hGH fusion gene was expressed under the control of the xyl promoter of pTX15. The expression was obtained, after the inactivation of XylR, the repressor of the xyl promoter, by the addition of 0.5% xylose to the nutrient medium. The in vitro cloning and sequencing were carried out by standard methods (1). The expression of the hGH gene was performed as a fusion with the lip-signal and propeptide from *Staphylococcus hyicus*, which contains an enterokinase cutting site which allows the release of the mature hGH with the correct N-terminus from the fusion protein (FIG. 1). The resulting expression vector pTX-LipP-hGH4 is identical to the vector pTX-LipP-hGH2 apart from the codon use of the mature hGH. The *S. carnosus* strains containing one of the plasmids were cultivated in a modified LB medium (1% soya bean extract, 0.5% yeast extract, 0.5% NaCl) supplemented with 0.5% xylose, to activate the xyl promoter of the expression vectors. The use of the improved hGH DNA had a profound effect on the efficiency of the production of hGH in *S. carnosus*. The Lip-hGH yield was improved at least twofold and the amount of shortened Lip-hGH protein was significantly reduced (FIG. 2, traces 2 and 3). The shortened Lip-hGH proteins are not the result of extracellular proteolytic activities, as the Lip-hGH protein is stable in the *S. carnosus* supernatant. The reduced presence of the shortened proteins in the supernatant of *S. carnosus* (pTX-LipP-hGH4) shows that hGH is translated faster by the optimised DNA sequence and thus gives intracellular proteases less opportunity to cut up the protein before it is secreted away through the cytoplasmic membrane.

EXAMPLE 2

Coexpression of t-RNAs Specific for Rare Codons in hGH cDNA

The arginine codon AGG is extremely rare in *S. carnosus* genes, as it is used in only 0.8% of the arginine codons. The corresponding tRNA genes in *S. carnosus* have not yet been identified. Therefore, we expressed *E. coli* tRNAs for the AGG codon in *S. carnosus*. The *E. coli* genes argU and argW, which code the tRNAs for the codons AGG/AGA and AGG, had been cloned with their natural promoters and terminators into the plasmids pUBS520 or pSB101 (2, 16). The fragments were isolated as SalI-SphI (argu) and XmaI-EcoRI (argw) fragments and cloned into the corresponding restriction cutting sites of the shuttle (transfer) vector pRB572 (4). The resulting plasmids pRBargU and pRBargW were transformed in *S. carnosus* (pTX-LipP-hGH2), which express hGH cDNA.

The protein patterns in the supernatant of the *S. carnosus* strains obtained are comparable with *S. carnosus* (pTX-LipP-hGH4) with increased production of the Lip-hGH protein and less truncated proteins. Therefore, the expression of rare tRNAs according to the invention has advantageous properties for the preparation of human proteins in *S. carnosus*, for example.

LEGEND RELATING TO THE FIGURES

FIG. 1. Expression of the Lip-hGH fusion in the plasmids pTX-LipP-hGH2 or pTX-LipP-hGH4. The gene fusion is made up of the DNA sequences coding for the signal peptide (SP) and the propeptide (PP) from *Staphylococcus hyicus* lipase and the hGH part of the mature protein (in black) and is transcribed by the xyl promoter (shown as a grey triangle). The hGH cDNA or the synthetic DNA sequence was inserted between the NsiI and the PstI cutting site. The 5' end pf the hGH DNA sequence was modified to code the enterokinase cutting site 'DDDK', followed by the mature hGH sequence, as shown underneath the gene.

FIG. 2. Detection of the Lip-hGH fusion proteins in the *S. carnosus* supernatant. Equal amounts of the supernatant were separated by SDS-PAGE on Tris-glycine gels containing 15% acrylamide and then stained with Coomassie Blue. The traces 1-5 contain supernatants of *S. carnosus* strains containing the empty control vector pTX16 (15), a derivative of pTX15 (trace 1), the plasmids pTX-LipP-hGH4 with the improved hGH gene (trace 2), pTX-LipP-hGH2 with the hGH cDNA (trace 3), pTX-LipP-hGH2 plus pRBargU (trace 4), and pTX-LipP-hGH2 plus pRBargW (trace 5). Standard proteins and their molecular weights (kDa) are shown on the left-hand side. The supernatants were concentrated by precipitation with trichloroacetic acid. SDS page was carried out by standard methods from the prior art.

FIGS. 3A and 3B. Nucleotide and amino acid sequence of the hGH according to the invention (LipPhGH4, SEQ: ID-No.3).

Relevant restriction cutting sites are underlined once, the Shine-Dalgarno sequence is underlined twice. The signal peptidase 1 and the enterokinase cleavage site in the are underlined with a broken line. Only the regions between the BglII and NdeI site and between the NsiI and the PstI site had been synthetically produced and optimised. The remainder consists of the original sequence of the signal and propeptide of the lipase from *Staphylococcus hyicus*.

Literature
1. Ausubel, F. M., R. Brent, R. E. Kingston, D. D. Moore, J. G. Seidman, J. A. Smith, and K. Struhl. 1990. Current protocols in molecular biology. John Wiley and Sons, Inc., New York, N.Y.
2. Brinkmann, U., R. E. Mattes, and P. Buckel. 1989. High-level expression of recombinant genes in *Eschericia coli* is dependent on the availability of the dnaY gene product. Gene. 85:109–114.
3. Brosius, J. 1989. Superpolylinkers in cloning and expression vectors. DNA. 8:759–777.
4. Brückner, R. 1992. A series of shuttle vectors for *Bacillus subtilis* and *Escherichia coli*. Gene. 122:187–192.
5. Cano, F., S. Liljeqvist, T. N. Nguyen, P. Samuelson, J. Y. Bonnefoy, S. Stahl, and A. Robert. 1999. A surface-displayed cholera toxin B peptide improves antibody response using food-grade staphylococci for mucosal subunit vaccine delivery. FEMS Immunol. Med. Microbiol. 25:289–298.
6. Del Tito, B. J., J. M. Ward, C. J. L. Hodgson, C. Gershater, H. Edwards, L. A. Wysocki, F. A. Watson, G. Sathe, and J. F. Kane. 1995. Effects of a minor isoleucyl tRNA on heterologous protein translation in *Escherichia coli*. J. Bacteriol. 177:7086–7091.
7. Demleitner, G., and F. Götz. 1994. Evidence for importance of the *Staphylococcus hyicus* lipase pro-peptide in lipase secretion, stability and activity. FEMS Microbiol. Lett. 121:189–198.
8. Gilbert, M., R. Morosoli, F. Shareck, and D. Kluepfel. 1995. Production and secretion of proteins by streptomycetes. Crit. Rev. Biotechnol. 15:13–39.
9. Götz, F. 1990. Development of a cloning system in *Staphylococcus carnosus*: Different processing of the *Staphylococcus hyicus* lipase in *Staphylococcus camosus* and *Staphylococcus hyicus*, p. 273–281. In R. P. Novick (ed.), Molecular biology of the staphylococci. VCH Publisher Inc., New York, N.Y.
10. Götz, F. 1990. *Staphylococcus carnosus*: a new host organism for gene cloning and protein production. J. Appl. Bacteriol. Symp. Suppl.:49S-53S.
11. Götz, F., and B. Schumacher. 1987. Improvements of protoplast transformation in *Staphylococcus carnosus*. FEMS Microbiol. Lett. 40:285–288.
12. Liljeqvist, S., F. Cano, T. N. Nguyen, M. Uhlen, A. Robert, and S. Stahl. 1999. Surface display of functional fibronectin-binding domains on *Staphylococcus carnosus*. FEBS Lett. 446:299–304.
13. Makrides, S. C. 1996. Strategies for achieving high-level expression of genes in *Escherichia coli*. Microbiol. Reviews. 60:512–538.
14. Nikoleit, K., R. Rosenstein, H. M. Verheij, and F. Götz. 1995. Comparative biochemical and molecular analysis of the *Staphylococcus hyicus, Staphylococcus aureus* and a hybrid lipase. Eur. J. Biochem 228:732–738.
15. Peschel, A., B. Ottenwälder, and F. Götz. 1996. Inducible production and cellular location of the epidermin biosynthetic enzyme EpiB using an improved staphylococcal expression system. FEMS Microbiol. Lett. 137:279–284.
16. Schenk, P. M., S. Baumann, R. Mattes, and H. H. Steinbiss. 1995. Improved high level expression system for eucaryotic genes in *Escherichia coli* using T7 RNA polymerase and rare Arg-tRNAs.
17. Thumm, G., and F. Götz. 1997. Studies on prolysostaphin processing and characterization of the lysostaphin immununity factor (Lif) of *Staphylococcus simulans* biovar staphylolyticus. Mol. Microbiol. 23:1251–1265.
18. Vance, M. L., and N. Mauras. 1999. Growth hormone therapy in adults and children. New Engl. J. Med. 341:1206–1216.
19. Wong, S. L. 1995. Advances in the use of *Bacillus subtilis* for the expression and secretion of heterologous proteins. Curr. Opin. Biotechnol. 6:517–522.

What is claimed is:

1. A method for preparing a heterologous recombinant protein in a *S. carnosus* host cell comprising:
   (a) transforming said host cell with one or more nucleic acids which code for tRNA or tRNAs specific for codons with an average frequency of less than 15% in said host cell;
   (b) transforming said host cell of (a) with a nucleic acid coding for the heterologous recombinant protein; and
   (c) expressing said nucleic acid in (b).

2. An isolated nucleic acid molecule comprising the nucleotide sequence selected from the group consisting of SEQ ID NO: 1, NO:1 on the basis of the degenerate code.

3. The nucleic acid molecule according to claim 2, comprising SEQ ID:1.

4. A vector comprising the nucleic acid molecule according to claim 2.

5. A host cell comprising the nucleic acid molecule according to claim 2.

6. A host cell comprising the vector according to claim 4.

7. A recombinant host cell selected from the genus Staphylococcus transformed with one or more tRNA molecules or the nucleic acid coding therefor, which code for codons used in the host cell with an average frequency of less than 15%.

8. The host cell according to claim 6, wherein said host cell is selected from the genus Staphylococcus.

9. The host cell according to claim 8, wherein said host cell is *Staphylococcus carnosus*.

10. The host cell according to claim 7, wherein said host cell is *Staphylococcus carnosus*.

11. The method of claim 1, wherein said nucleic acid in (a) encodes AGG-t-RNA or AGA-t-RNA.

12. A method for preparing a heterologous recombinant protein in *S. carnosus* host cell comprising:
 (a) replacing in a nucleic acid encoding the heterologous recombinant protein, at least one codon with an average frequency of less than 15% in the host cell with at least one codon with an average frequency of at least 15%;
 (b) transforming the host cell with said nucleic acid; and
 (c) expressing said nucleic acid in (b).

13. The method according to claim 12, wherein said recombinant protein is an antibody.

14. The method according to claim 12, wherein said recombinant protein is insulin.

15. The method according to claim 12, wherein said recombinant protein is tissue plasminogen activator (tPa).

16. The method according to claim 12, wherein said recombinant protein is a human protein.

17. The method according to claim 12, wherein said recombinant protein is a growth hormone.

18. The method according to claim 12, wherein said recombinant protein is a human growth hormone.

19. The method according to claim 12, wherein G- or C-rich codons are replaced by codons containing A or T.

20. The method according to claim 12, wherein codon GCC is replaced by codon GCA.

21. The method according to claim 12, wherein codon TGC is replaced by codon TGT.

22. The method according to claim 12, wherein codon GAC is replaced by codon GAT.

23. The method according to claim 12, wherein codon GAG is replaced by codon GAA.

24. The method according to claim 12, wherein codon TTC is replaced by codon TTT.

25. The method according to claim 12, wherein codon GGG is replaced by codon GGT.

26. The method according to claim 12, wherein codon CAC is replaced by codon CAT.

27. The method according to claim 12, wherein codon ATA is replaced by codon ATT.

28. The method according to claim 12, wherein codon AAG is replaced by codon AAA.

29. The method according to claim 12, wherein codon CTC is replaced by codon TTA.

30. The method according to claim 12, wherein codon AAC is replaced by codon AAT.

31. The method according to claim 12, wherein codon CCC is replaced by codon CCA.

32. The method according to claim 12, wherein codon CAG is replaced by codon CAA.

33. The method according to claim 12, wherein codon CGG is replaced by codon CGT.

34. The method according to claim 12, wherein codon TCG is replaced by codon TCA.

35. The method according to claim 12, wherein codon ACC is replaced by codon ACA.

36. The method according to claim 12, wherein codon GTC is replaced by codon GTT.

37. The method according to claim 12, wherein codon TAC is replaced by codon TAT.

38. The method according to claim 12, wherein codon IGA is replaced by codon TAA.

39. A method for preparing a heterologous recombinant protein in a prokaryotic host cell comprising:
 (a) replacing at least one codon in a nucleic acid coding for the heterologous recombinant protein with an average frequency of less than 15% in the host cell with a codon with an average frequency of at least 15%;
 (b) transforming the host cell with said nucleic acid;
 (c) further transforming the host cell with one or more nucleic acids which code for tRNA or tRNAs specific for codons used in the host cell with an average frequency of less than 15%; and
 (d) expressing said nucleic acid in (k) (e) and said nucleic acid in (c).

40. The method according to claim 39, wherein said host cell is *E. coli*.

41. The method according to claim 39, wherein said host cell is a host cell selected from the genus Staphylococcus.

42. The method according to claim 41, wherein said host cell is a *S. carnosus*.

43. The method according to claim 39, wherein said recombinant protein is an antibody.

44. The method according to claim 39, wherein said recombinant protein is insulin.

45. The method according to claim 39, wherein said recombinant protein is tissue plasminogen activator (tPa).

46. The method according to claim 39, wherein said recombinant protein is a human protein.

47. The method according to claim 39, wherein said recombinant protein is a growth hormone.

48. The method according to claim 39, wherein said recombinant protein is a human growth hormone.

49. The method according to claim 39, wherein G- or rich codons are replaced by codons containing A or T.

50. The method according to claim 39, wherein codon GCC is replaced by codon GCA.

51. The method according to claim 39, wherein codon TGC is replaced by codon TGT.

52. The method according to claim 39, wherein codon GAC is replaced by codon GAT.

53. The method according to claim 39, wherein codon GAG is replaced by codon GAA.

54. The method according to claim 39, wherein codon TTC is replaced by codon TTT.

55. The method according to claim 39, wherein codon GGG is replaced by GGT.

56. The method according to claim 39, wherein codon CAC is replaced by codon CAT.

57. The method according to claim 39, wherein codon ATA is replaced by codon ATT.

58. The method according to claim 39, wherein codon AAG is replaced by codon AAA.

59. The method according to claim 39, wherein codon CTC is replaced by codon TTA.

60. The method according to claim 39, wherein codon AAC is replaced by codon AAT.

61. The method according to claim 39, wherein codon CCC is replaced by codon CCA.

62. The method according to claim 39, wherein codon CAG is replaced by codon CAA.

63. The method according to claim 39, wherein codon CGG is replaced by codon CGT.

64. The method according to claim 39, wherein codon TCG is replaced by codon TCA.

65. The method according to claim 39, wherein codon ACC is replaced by codon ACA.

66. The method according to claim 39, wherein codon GTC is replaced by codon GTT.

67. The method according to claim 39, wherein codon TAC is replaced by codon TAT.

68. The method according to claim 39, wherein codon TGA is replaced by codon TAA.

69. The method according to claim 39, wherein said host cell is transformed with the nucleic acid coding for AGG-tRNA or AGA-tRNA.

70. A nucleic acid coding for human growth hormone hGH which is expressed in a *S. carnosus* host cell, wherein at least one codon that is used in the *S. carnosus* host cell with an average frequency of less than 15% is replaced by at least one codon with an average frequency of at least 15%.

71. A nucleic acid coding for human growth hormone hGH which is expressed in a *S. carnosus* host cell, wherein at least one codon that is used in the host cell with an average frequency of less than 10% is replaced by at least one codon with an average frequency of at least 10%.

72. A nucleic acid coding for human growth hormone hGH which is expressed in a *S. carnosus* host cell, wherein at least one codon that is used in the *S. carnosus* host cell with an average frequency of less than 7% is replaced by at least one codon with an average frequency of at least 7%.

73. The method according to claim 1, further comprising determining the codon use of said host cell for host genes prior to step (a).

74. The method according to claim 1, wherein said host cell of step (a) is transformed with one or more nucleic acids which code for tRNA or tRNAs specific for codons with an average frequency of less than 10% in said host cell.

75. The method according to claim 1, wherein said host cell of step (a) is transformed with one or more nucleic acids which code for tRINA or tRINAs specific for codons with an average frequency of less than 7% in said host cell.

76. The host cell of claim 7, wherein said host cell is transformed with one or more tRNA molecules or the nucleic acid coding therefor, which codes for codons used in the host cell with an average frequency of less than 10%.

77. The host cell of claim 7, wherein said host cell is transformed with one or more tRNA molecules or the nucleic acid coding therefor, which codes for codons used in the host cell with an average frequency of less than 7%.

78. The method according to claim 12, further comprising determining the codon use of the host cell for host genes prior to step (a).

79. The method according to claim 12, wherein all codons with an average frequency of less than 15% in the host cell are replaced with codons with an average frequency of at least 15%.

80. A method for preparing a heterologous recombinant protein in *S. carnosus* host cell comprising:
(a) replacing in a nucleic acid encoding the heterologous recombinant protein, at least one codon with an average frequency of less than 10% in the host cell with at least one codon with an average frequency of at least 10%;
(b) transforming the host cell with said nucleic acid; and
(c) expressing said nucleic acid in (b).

81. The method according to claim 80, wherein all codons with an average frequency of less than 10% in the host cell are replaced with codons with an average frequency of at least 10%.

82. A method for preparing a heterologous recombinant protein in *S. carnosus* host cell comprising:
(a) replacing in a nucleic acid encoding the heterologous recombinant protein, at least one codon with an average frequency of less than 7% in the host cell with at least one codon with an average frequency of at least 7%;
(b) transforming the host cell with said nucleic acid; and
(c) expressing said nucleic acid in (b).

83. The method according to claim 82, wherein all codons with an average frequency of less than 7% in the host cell are replaced with codons with an average frequency of at least 7%.

84. The method according to claim 39, further comprising determining the codon use of the host cell for host genes prior to step (a).

85. A method for preparing a heterologous recombinant protein in a prokaryotic host cell comprising:
(a) replacing at least one codon in a nucleic acid coding for the heterologous recombinant protein with an average frequency of less than 10% in the host cell with a codon with an average frequency of at least 10%;
(b) transforming the host cell with said nucleic acid;
(c) further transforming the host cell with one or more nucleic acids which code for tRNA or tRNAs specific for codons used in the host cell with an average frequency of less than 10%; and
(d) expressing said nucleic acid in (b) and said nucleic acid in (c).

86. A method for preparing a heterologous recombinant protein in a prokaryotic host cell comprising:
(a) replacing at least one codon in a nucleic acid coding for the heterologous recombinant protein with an average frequency of less than 7% in the host cell with a codon with an average frequency of at least 7%;
(b) transforming the host cell with said nucleic acid;
(c) further transforming the host cell with one or more nucleic acids which code for tRNA or tRNAs specific for codons used in the host cell with an average frequency of less than 7%; and
(d) expressing said nucleic acid in (b) and said nucleic acid in (c).

87. The method according to claim 85, further comprising determining the codon use of the host cell for host genes prior to step (a).

88. The method according to claim 86, further comprising determining the codon use of the host cell for host genes prior to step (a).

* * * * *

SEQUENCE LISTING

<160> NUMBER OF SEQ ID NOS: 3

<210> SEQ ID NO 1
<211> LENGTH: 1383
<212> TYPE: DNA
<213> ORGANISM: Homo sapiens
<220> FEATURE:
<221> NAME/KEY: misc_feature
<222> LOCATION: (1)..(2)
<223> OTHER INFORMATION: May be any nucleotide

<400> SEQUENCE: 1

```
nnagatctaa aggaggtaat tcatatgaaa gaaacaaaac atcaacacac attttctatc      60
cgtaagtcgg cttatggtgc cgcgtcggtt atggtcgcat catgtatatt tgtcatcggt     120
gggggcgtgg cagaggcaaa tgattcgaca acacaaacaa cgacaccact agaagtcgct     180
caaacgtcgc agcaagaaac acatacacat caaacacctg ttacatcatt acatactgca     240
acacctgaac atgttgatga ctctaaagaa gcaacacctt tacctgaaaa agcagagtca     300
ccaaaaaccg aagtgacagt tcaaccttca tcgcatacac aggaagtacc tgcgttacat     360
aaaaaaacac agcaacaacc ggcgtataag gataaaacgg taccagagtc aacgatagca     420
tcaaagtcgg ttgaatcaaa taagcaaca gaaaatgaga tgtcacctgt tgaacatcat     480
gcttcaaatg tggaaaaacg tgaagataga ttggagacta atgagacaac accgccatca     540
gtggaccgtg aatttagcca taaaatcatc aataatacgc acgtaaatcc aaaaacggat     600
ggacaaacaa acgttaatgt tgatacgaaa acgatagaca ccgtttcacc gaaagatgac     660
agaatagata cggcgcaacc gaaacaagtc gacgttccta agaaaaatac aacggcacaa     720
aataaattta catcacaagc gagcgacaaa aaaccaacag taaaagatgc atcaggtggt     780
gatgatgatg ataaatttcc aacaattccc ttaagtcgat tgttcgataa cgctatgtta     840
cgtgcacata gattacacca gctagcattc gatacttatc aagaatttga ggaagcttac     900
atcccaaaag aacaaaagta tagcttttta caaaatccgc aaacatcatt atgtttctct     960
gaatcaattc caacacctag taaccgtgag gaaactcagc aaaaatcaaa tttagaactt    1020
ttacgtatta gcttgttact tatacaatct tggttagaac cagttcaatt tttacgttca    1080
gtattcgcaa atagtttagt ctatggtgct tcagactcta acgtatacga tttattgaaa    1140
gacttagaag aaggaattca aacattaatg ggtcgtttgg aagatggttc accaagaact    1200
ggccaaattt taaacaaac atatagcaaa ttcgatacta attcacataa cgatgacgca    1260
ttacttaaaa attacggttt attgtattgt tttcgtaaag atatggataa agttgaaaca    1320
ttcttacgca tagtacaatg ccgttctgtt gaaggatcat gtggttttta atgataactg    1380
cag                                                                 1383
```

<210> SEQ ID NO 2
<211> LENGTH: 448
<212> TYPE: PRT
<213> ORGANISM: Homo Sapiens

<400> SEQUENCE: 2

```
Met Lys Glu Thr Lys His Gln His Thr Phe Ser Ile Arg Lys Ser Ala
1               5                   10                  15

Tyr Gly Ala Ala Ser Val Met Val Ala Ser Cys Ile Phe Val Ile Gly
            20                  25                  30

Gly Gly Val Ala Glu Ala Asn Asp Ser Thr Thr Gln Thr Thr Thr Pro
```

-continued

```
            35                  40                  45
Leu Glu Val Ala Gln Thr Ser Gln Gln Glu Thr His Thr His Gln Thr
     50                  55                  60

Pro Val Thr Ser Leu His Thr Ala Thr Pro Glu His Val Asp Asp Ser
 65                  70                  75                  80

Lys Glu Ala Thr Pro Leu Pro Glu Lys Ala Glu Ser Pro Lys Thr Glu
                 85                  90                  95

Val Thr Val Gln Pro Ser Ser His Thr Gln Glu Val Pro Ala Leu His
                100                 105                 110

Lys Lys Thr Gln Gln Gln Pro Ala Tyr Lys Asp Lys Thr Val Pro Glu
            115                 120                 125

Ser Thr Ile Ala Ser Lys Ser Val Glu Ser Asn Lys Ala Thr Glu Asn
    130                 135                 140

Glu Met Ser Pro Val Glu His His Ala Ser Asn Val Glu Lys Arg Glu
145                 150                 155                 160

Asp Arg Leu Glu Thr Asn Glu Thr Thr Pro Pro Ser Val Asp Arg Glu
                165                 170                 175

Phe Ser His Lys Ile Ile Asn Asn Thr His Val Asn Pro Lys Thr Asp
            180                 185                 190

Gly Gln Thr Asn Val Asn Val Asp Thr Lys Thr Ile Asp Thr Val Ser
        195                 200                 205

Pro Lys Asp Asp Arg Ile Asp Thr Ala Gln Pro Lys Gln Val Asp Val
    210                 215                 220

Pro Lys Glu Asn Thr Thr Ala Gln Asn Lys Phe Thr Ser Gln Ala Ser
225                 230                 235                 240

Asp Lys Lys Pro Thr Val Lys Asp Ala Ser Gly Gly Asp Asp Asp Asp
                245                 250                 255

Lys Phe Pro Thr Ile Pro Leu Ser Arg Leu Phe Asp Asn Ala Met Leu
            260                 265                 270

Arg Ala His Arg Leu His Gln Leu Ala Phe Asp Thr Tyr Gln Glu Phe
        275                 280                 285

Glu Glu Ala Tyr Ile Pro Lys Glu Gln Lys Tyr Ser Phe Leu Gln Asn
    290                 295                 300

Pro Gln Thr Ser Leu Cys Phe Ser Glu Ser Ile Pro Thr Pro Ser Asn
305                 310                 315                 320

Arg Glu Glu Thr Gln Gln Lys Ser Asn Leu Glu Leu Arg Ile Ser
                325                 330                 335

Leu Leu Leu Ile Gln Ser Trp Leu Glu Pro Val Gln Phe Leu Arg Ser
            340                 345                 350

Val Phe Ala Asn Ser Leu Val Tyr Gly Ala Ser Asp Ser Asn Val Tyr
        355                 360                 365

Asp Leu Leu Lys Asp Leu Glu Glu Gly Ile Gln Thr Leu Met Gly Arg
    370                 375                 380

Leu Glu Asp Gly Ser Pro Arg Thr Gly Gln Ile Phe Lys Gln Thr Tyr
385                 390                 395                 400

Ser Lys Phe Asp Thr Asn Ser His Asn Asp Asp Ala Leu Leu Lys Asn
                405                 410                 415

Tyr Gly Leu Leu Tyr Cys Phe Arg Lys Asp Met Asp Lys Val Glu Thr
            420                 425                 430

Phe Leu Arg Ile Val Gln Cys Arg Ser Val Glu Gly Ser Cys Gly Phe
        435                 440                 445

<210> SEQ ID NO 3
```

-continued

```
<211> LENGTH: 1383
<212> TYPE: DNA
<213> ORGANISM: Artificial Sequence
<220> FEATURE:
<223> OTHER INFORMATION: Homo sapiens DNA sequence flanked by vectorial
      DNA sequence
<221> NAME/KEY: misc_feature
<222> LOCATION: (1)..(2)
<223> OTHER INFORMATION: May be any nucleotide

<400> SEQUENCE: 3
nnagatctaa aggaggtaat tcatatgaaa gaaacaaaac atcaacacac attttctatc      60
cgtaagtcgg cttatggtgc cgcgtcggtt atggtcgcat catgtatatt tgtcatcggt     120
gggggcgtgg cagaggcaaa tgattcgaca acacaaacaa cgacaccact agaagtcgct     180
caaacgtcgc agcaagaaac acatacacat caaacacctg ttacatcatt acatactgca     240
acacctgaac atgttgatga ctctaaagaa gcaacacctt tacctgaaaa agcagagtca     300
ccaaaaaccg aagtgacagt tcaaccttca tcgcatacac aggaagtacc tgcgttacat     360
aaaaaaacac agcaacaacc ggcgtataag gataaaacgg taccagagtc aacgatagca     420
tcaaagtcgg ttgaatcaaa taaagcaaca gaaaatgaga tgtcacctgt tgaacatcat     480
gcttcaaatg tggaaaaacg tgaagataga ttggagacta atgagacaac accgccatca     540
gtggaccgtg aatttagcca taaaatcatc aataatacgc acgtaaatcc aaaaacggat     600
ggacaaacaa acgttaatgt tgatacgaaa acgatagaca ccgtttcacc gaaagatgac     660
agaatagata cggcgcaacc gaaacaagtc gacgttccta aagaaaatac aacggcacaa     720
aataaattta catcacaagc gagcgacaaa aaaccaacag taaaagatgc atcaggtggt     780
gatgatgatg ataaatttcc aacaattccc ttaagtcgat tgttcgataa cgctatgtta     840
cgtgcacata gattacacca gctagcattc gatacttatc aagaatttga ggaagcttac     900
atcccaaaag aacaaaagta tagcttttta caaaatccgc aaacatcatt atgtttctct     960
gaatcaattc caacacctag taaccgtgag gaaactcagc aaaaatcaaa tttagaactt    1020
ttacgtatta gcttgttact tatacaatct tggttagaac cagttcaatt tttacgttca    1080
gtattcgcaa atagtttagt ctatggtgct tcagactcta acgtatacga tttattgaaa    1140
gacttagaag aaggaattca aacattaatg ggtcgtttgg aagatggttc accaagaact    1200
ggccaaattt ttaaacaaac atatagcaaa ttcgatacta attcacataa cgatgacgca    1260
ttacttaaaa attacggttt attgtattgt tttcgtaaag atatggataa agttgaaaca    1320
ttcttacgca tagtacaatg ccgttctgtt gaaggatcat gtggttttta atgataactg    1380
cag                                                                  1383
```